United States Patent
Fütterer et al.

(10) Patent No.: US 7,550,419 B2
(45) Date of Patent: Jun. 23, 2009

(54) MONO-, DI- AND POLYOL ALKOXYLATE PHOSPHATE ESTERS IN ORAL CARE FORMULATIONS AND METHODS FOR USING SAME

(75) Inventors: Tobias Johannes Fütterer, Singapore (SG); Lawrence Alan Hough, Philadelphia, PA (US); Robert Lee Reierson, Princeton Junction, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 12/137,647

(22) Filed: Jun. 12, 2008

(65) Prior Publication Data

US 2008/0311055 A1 Dec. 18, 2008

Related U.S. Application Data

(60) Provisional application No. 60/943,490, filed on Jun. 12, 2007.

(51) Int. Cl.
*C11D 7/36* (2006.01)
*C11D 3/37* (2006.01)

(52) U.S. Cl. .......... 510/137; 510/130; 510/131; 510/136; 510/150; 510/228; 510/236; 510/288; 510/319; 510/158; 510/347; 510/390; 510/423; 510/431; 510/436; 510/467; 424/48; 424/49; 424/57; 424/401; 524/900; 524/901; 524/902

(58) Field of Classification Search .......... 510/130, 510/131, 136, 137, 139, 150, 158, 228, 236, 510/288, 319, 347, 390, 423, 431, 436, 467
See application file for complete search history.

(56) References Cited

U.S. PATENT DOCUMENTS

| | | |
|---|---|---|
| 2,438,091 A | 3/1948 | Lynch |
| 2,524,218 A | 10/1950 | Bersworth |
| 2,528,378 A | 10/1950 | Mannheimer |
| 2,530,147 A | 11/1950 | Bersworth |
| 2,658,072 A | 11/1953 | Kosmin |
| 2,826,551 A | 3/1958 | Geen |
| 2,874,074 A | 2/1959 | Johnson |
| 2,946,725 A | 7/1960 | Norris et al. |
| 3,033,704 A | 5/1962 | Sherrill et al. |
| 3,070,510 A | 12/1962 | Cooley et al. |
| 3,244,724 A | 4/1966 | Guttmann |
| 3,308,067 A | 3/1967 | Diehl |
| 3,332,880 A | 7/1967 | Kessler et al. |
| 3,538,230 A | 11/1970 | Pader et al. |
| 3,553,139 A | 1/1971 | McCarty |
| 3,598,865 A | 8/1971 | Lew |
| 3,599,716 A | 8/1971 | Thompson |
| 3,678,154 A | 7/1972 | Widder et al. |
| 3,681,241 A | 8/1972 | Rudy |
| 3,717,630 A | 2/1973 | Booth |
| 3,723,322 A | 3/1973 | Diehl |
| 3,793,209 A | 2/1974 | Thompson |
| 3,850,831 A | 11/1974 | Hellsten et al. |
| 3,862,307 A | 1/1975 | Di Giulio |
| 3,869,412 A | 3/1975 | Waag |
| 3,893,929 A | 7/1975 | Basadur |
| 3,912,681 A | 10/1975 | Dickson |
| 3,939,911 A | 2/1976 | Maddox, Jr. et al. |
| 3,948,838 A | 4/1976 | Hinton, Jr. et al. |
| 3,956,198 A | 5/1976 | Bauer |
| 3,959,230 A | 5/1976 | Hays |
| 3,959,458 A | 5/1976 | Agricola et al. |
| 3,964,500 A | 6/1976 | Drakoff |
| 3,976,586 A | 8/1976 | Chakrabarti |
| 4,001,133 A | 1/1977 | Sorgenfrei et al. |
| 4,008,165 A | 2/1977 | Maddox, Jr. et al. |
| 4,017,410 A | 4/1977 | Sorgenfrei et al. |
| 4,038,027 A | 7/1977 | Kearney |
| 4,049,558 A | 9/1977 | Rasmussen |
| 4,051,234 A | 9/1977 | Gieske et al. |
| 4,101,457 A | 7/1978 | Place et al. |
| 4,116,984 A | 9/1978 | Prinzbach et al. |
| 4,127,489 A | 11/1978 | Pracht et al. |
| 4,144,226 A | 3/1979 | Crutchfield et al. |
| 4,146,495 A | 3/1979 | Crutchfield et al. |
| 4,152,416 A | 5/1979 | Spitzer et al. |
| 4,152,421 A | 5/1979 | Tsutsumi et al. |
| 4,206,215 A | 6/1980 | Bailey |

(Continued)

FOREIGN PATENT DOCUMENTS

| | | |
|---|---|---|
| DE | 2829022 | 1/1980 |
| EP | 0011984 | 6/1980 |
| EP | 0066915 | 12/1982 |
| EP | 0132043 | 1/1985 |
| EP | 0132046 | 1/1985 |
| EP | 0219048 | 4/1987 |
| EP | 0488868 | 6/1992 |
| EP | 0561656 | 9/1993 |
| EP | 0909809 | 4/1999 |
| EP | 1196523 | 4/2002 |

(Continued)

OTHER PUBLICATIONS

U.S. Appl. No. 12/137,589 "Mono-, Di- and Polyol Phosphate Esters in Personal Care Formulations", Futterer et al., filed Jun. 12, 2008.
U.S. Appl. No. 12/137,823 "Method for Recovering Crude Oil from a Subterranean Formation", Futterer et al., filed Jun. 12, 2008.

(Continued)

*Primary Examiner*—Charles I Boyer
(74) *Attorney, Agent, or Firm*—Novak Druce + Quigg LLP

(57) ABSTRACT

This invention relates to a composition useful as an oral care composition comprising an organophosphate material, additional oral care composition ingredients, for example, a surfactant agent, and optionally an abrasive agent.

34 Claims, 3 Drawing Sheets

U.S. PATENT DOCUMENTS

| | | | |
|---|---|---|---|
| 4,235,735 A | 11/1980 | Marco et al. |
| 4,240,919 A | 12/1980 | Chapman |
| 4,261,868 A | 4/1981 | Hora et al. |
| 4,264,580 A | 4/1981 | Barberio |
| 4,278,129 A | 7/1981 | Walton |
| 4,287,080 A | 9/1981 | Siklosi |
| 4,321,256 A | 3/1982 | Hasegawa et al. |
| 4,350,680 A | 9/1982 | Harvey et al. |
| 4,364,837 A | 12/1982 | Pader |
| 4,391,722 A | 7/1983 | Schwartz et al. |
| 4,393,935 A | 7/1983 | Walton |
| 4,470,923 A | 9/1984 | Koster |
| 4,483,779 A | 11/1984 | Llenado et al. |
| 4,507,219 A | 3/1985 | Hughes |
| 4,525,291 A | 6/1985 | Smith et al. |
| 4,536,317 A | 8/1985 | Llenado et al. |
| 4,536,318 A | 8/1985 | Cook et al. |
| 4,536,319 A | 8/1985 | Payne |
| 4,541,483 A | 9/1985 | Walton |
| 4,548,744 A | 10/1985 | Connor |
| 4,557,853 A | 12/1985 | Collins |
| 4,559,056 A | 12/1985 | Leigh et al. |
| 4,565,647 A | 1/1986 | Llenado |
| 4,579,681 A | 4/1986 | Ruppert et al. |
| 4,597,898 A | 7/1986 | Vander Meer |
| 4,599,188 A | 7/1986 | Llenado |
| 4,614,519 A | 9/1986 | Ruppert et al. |
| 4,627,977 A | 12/1986 | Gaffar et al. |
| 4,664,839 A | 5/1987 | Rieck |
| 4,702,857 A | 10/1987 | Gosselink |
| 4,711,730 A | 12/1987 | Gosselink et al. |
| 4,721,580 A | 1/1988 | Gosselink |
| 4,728,455 A | 3/1988 | Rerek |
| 4,734,099 A | 3/1988 | Cyprien |
| 4,746,456 A | 5/1988 | Kud et al. |
| 4,752,409 A | 6/1988 | Drapier et al. |
| 4,770,666 A | 9/1988 | Clauss |
| 4,801,395 A | 1/1989 | Chazard et al. |
| 4,813,482 A | 3/1989 | Walton |
| 4,836,949 A | 6/1989 | Klajnscek |
| 4,859,358 A | 8/1989 | Gabriel et al. |
| 4,877,896 A | 10/1989 | Maldonado et al. |
| 4,886,609 A | 12/1989 | Walton |
| 4,891,160 A | 1/1990 | Vander Meer |
| 4,894,220 A | 1/1990 | Nabi et al. |
| 4,902,499 A | 2/1990 | Bolish, Jr. et al. |
| 4,933,101 A | 6/1990 | Cilley et al. |
| 4,968,451 A | 11/1990 | Scheibel et al. |
| 4,976,879 A | 12/1990 | Maldonado et al. |
| 5,015,466 A | 5/1991 | Parran, Jr. et al. |
| 5,019,373 A | 5/1991 | Carter et al. |
| 5,038,864 A | 8/1991 | Dunleavy |
| 5,064,553 A | 11/1991 | Dixit et al. |
| 5,098,590 A | 3/1992 | Dixit et al. |
| 5,104,643 A | 4/1992 | Grollier et al. |
| 5,114,606 A | 5/1992 | van Vliet et al. |
| 5,130,043 A | 7/1992 | Prince et al. |
| 5,160,450 A | 11/1992 | Okahara et al. |
| 5,236,615 A | 8/1993 | Trinh et al. |
| 5,280,117 A | 1/1994 | Kerschner et al. |
| 5,332,528 A | 7/1994 | Pan et al. |
| 5,370,865 A | 12/1994 | Yamagishi et al. |
| 5,405,542 A | 4/1995 | Trinh et al. |
| 5,413,727 A | 5/1995 | Drapier et al. |
| 5,415,807 A | 5/1995 | Gosselink et al. |
| 5,415,860 A | 5/1995 | Beucherie et al. |
| 5,510,042 A | 4/1996 | Hartman et al. |
| 5,510,306 A | 4/1996 | Murray |
| 5,534,197 A | 7/1996 | Scheibel et al. |
| 5,550,274 A | 8/1996 | Reierson |
| 5,554,781 A | 9/1996 | Reierson |
| 5,559,261 A | 9/1996 | Sivik |
| 5,565,145 A | 10/1996 | Watson et al. |
| 5,573,709 A | 11/1996 | Wells |
| 5,607,680 A | 3/1997 | Brissonnet et al. |
| 5,648,584 A | 7/1997 | Murray |
| 5,648,585 A | 7/1997 | Murray et al. |
| 5,686,024 A | 11/1997 | Dahanayake et al. |
| 5,710,121 A | 1/1998 | Tracy et al. |
| 5,798,326 A | 8/1998 | Goldstein et al. |
| 5,804,542 A | 9/1998 | Scheper et al. |
| 5,824,289 A * | 10/1998 | Stoltz ......................... 424/45 |
| 5,849,960 A | 12/1998 | Singleton et al. |
| 5,853,710 A | 12/1998 | Dehan et al. |
| 5,858,343 A | 1/1999 | Szymczak |
| 5,879,469 A | 3/1999 | Avram |
| 5,902,574 A | 5/1999 | Stoner et al. |
| 5,902,778 A | 5/1999 | Hartmann et al. |
| 5,939,052 A | 8/1999 | White, Jr. et al. |
| 5,968,893 A | 10/1999 | Manohar et al. |
| 6,017,936 A | 1/2000 | Polson et al. |
| 6,136,221 A | 10/2000 | Reierson |
| 6,149,693 A | 11/2000 | Geib |
| 6,150,222 A | 11/2000 | Gardner et al. |
| 6,187,391 B1 | 2/2001 | Kataoka et al. |
| 6,220,352 B1 | 4/2001 | Walton |
| 6,222,077 B1 | 4/2001 | Singleton |
| 6,242,404 B1 | 6/2001 | Dahanayake et al. |
| 6,271,409 B1 | 8/2001 | Geib |
| 6,297,201 B1 | 10/2001 | Geib |
| 6,342,468 B1 | 1/2002 | Geib |
| 6,387,137 B1 | 5/2002 | Geib |
| 6,525,005 B1 | 2/2003 | Kravitz et al. |
| 6,566,313 B1 | 5/2003 | Hohenstein et al. |
| 6,569,261 B1 | 5/2003 | Aubay et al. |
| 6,579,466 B1 | 6/2003 | David et al. |
| 6,593,288 B2 | 7/2003 | Aubay et al. |
| 6,767,410 B2 | 7/2004 | Aubay et al. |
| 6,767,560 B2 | 7/2004 | Paek |
| 6,864,314 B1 | 3/2005 | Yeung et al. |
| 6,924,260 B2 | 8/2005 | Aubay |
| 7,262,153 B2 | 8/2007 | Shpakoff et al. |
| 7,381,695 B2 | 6/2008 | Minevski |
| 2003/0044469 A1 | 3/2003 | Viladot Petit et al. |
| 2003/0228339 A1 * | 12/2003 | El-Nokaly et al. .......... 424/401 |
| 2004/0185027 A1 | 9/2004 | Reierson et al. |
| 2004/0247534 A1 * | 12/2004 | Stoltz ......................... 424/52 |
| 2005/0020466 A1 | 1/2005 | Man et al. |
| 2005/0184273 A1 * | 8/2005 | Morelli et al. ......... 252/187.23 |
| 2006/0088482 A1 * | 4/2006 | Wulknitz et al. .............. 424/49 |
| 2006/0093559 A1 * | 5/2006 | Fabry ......................... 424/48 |
| 2006/0135384 A1 | 6/2006 | Luu et al. |
| 2006/0159631 A1 | 7/2006 | Buch et al. |
| 2006/0217286 A1 | 9/2006 | Geoffroy et al. |
| 2007/0145617 A1 * | 6/2007 | Finney et al. ................ 264/4.1 |
| 2007/0166243 A1 * | 7/2007 | Yoshida et al. ................ 424/49 |
| 2008/0028986 A1 | 2/2008 | Futterer et al. |
| 2008/0095719 A1 * | 4/2008 | Herrmann et al. ............. 424/48 |
| 2008/0220031 A1 * | 9/2008 | Wunsch et al. .............. 424/401 |

FOREIGN PATENT DOCUMENTS

| | | |
|---|---|---|
| EP | 1196527 | 4/2002 |
| EP | 1196528 | 4/2002 |
| FR | 2236926 | 2/1975 |
| FR | 2334698 | 7/1977 |
| GB | 849433 | 9/1960 |
| GB | 1314897 | 4/1973 |
| GB | 1475798 | 6/1977 |
| GB | 1498520 | 1/1978 |
| GB | 1537288 | 12/1978 |
| GB | 1578930 | 11/1980 |
| GB | 2 192 194 A | 1/1988 |
| GB | 2 283 036 A | 4/1995 |

| | | |
|---|---|---|
| GB | 2 283 755 A | 5/1995 |
| JP | 3157323 A1 | 7/1991 |
| JP | 047547 | 1/1992 |
| JP | 6313271 | 11/1994 |
| JP | 2003342140 A | 12/2003 |
| JP | 2005-013929 | 1/2005 |
| WO | 9532272 | 11/1995 |
| WO | 9532997 | 12/1995 |
| WO | 9623859 | 8/1996 |
| WO | 9623860 | 8/1996 |
| WO | 9623861 | 8/1996 |
| WO | 97/42287 A1 | 11/1997 |
| WO | 97/42288 A1 | 11/1997 |
| WO | 9742288 | 11/1997 |
| WO | 9838973 | 9/1998 |
| WO | 9841505 | 9/1998 |
| WO | 2004/082500 A2 | 9/2004 |

OTHER PUBLICATIONS

U.S. Appl. No. 12/137,738 "Hard Surface Cleaning Composition with Hydrophilizing Agent and Method for Cleaning Hard Surfaces", Futterer et al., filed Jun. 12, 2008.

U.S. Appl. No. 12/138,030 "Detergent Composition with Hydrophilizing Soil-Release Agent and Methods for Using Same" Futterer et al., filed Jun. 12, 2008.

Office Action mailed Oct. 3, 2008 in U.S. Appl. No. 12/138,030.

Office Action mailed Oct. 10, 2008 in U.S. Appl. No. 12/137,823.

Notice of Allowance mailed Oct. 29, 2008 in U.S. Appl. No. 12/137,589.

Notice of Allowance mailed Nov. 13, 2008 in U.S. Appl. No. 12/137,738.

* cited by examiner

Hexadecane
Pure DI Water
CaCO3 Crystal

Hexadecane
DI Water + PEG1000PE
CaCO3 Crystal

MONO-, DI- AND POLYOL ALKOXYLATE PHOSPHATE ESTERS IN ORAL CARE FORMULATIONS AND METHODS FOR USING SAME

CROSS REFERENCE TO RELATED APPLICATIONS

This claims the benefit of U.S. Provisional Patent Application No. 60/943,490 filed Jun. 12, 2007 and is incorporated by reference in its entirety.

FIELD OF THE INVENTION

This application relates to compositions useful in dentifrices and other oral care products. Particularly the invention relates to oral care compositions containing a surfactant agent consisting essentially of water soluble salts of monoalkyl and dialkyl phosphate esters. The invention includes oral care formulations including mono-, di-, and polyol phosphate esters as surface modification agents to change adhesion properties of these surfaces for hydrophobic as well as hydrophilic materials.

BACKGROUND OF THE INVENTION

The various benefits of using a variety of phosphate esters, as their salts, in oral care formulations have been reported for decades. U.S. Pat. No. 4,152,421 refers to the use of alkali metal or alkanolamine salts of alkyl phosphate esters in dentifrice formulations. It cites the high foaming property of the high monoalkyl content phosphate esters (monoalkyl:dialkyl phosphate, or MAP:DAP, weight ratio of 70:30-100:0) as novel, in combination with the "known" property of having no substantial after effects on the tastes and flavors of foods and drinks, especially citrus juices. The concept and range of structures is expanded in a subsequent patent, U.S. Pat. No. 5,370,865, which emphasizes the pleasant taste of basic amino acid salts, specifically with lysine, arginine and histidine. Another early patent, U.S. Pat. No. 4,264,580, covers the incorporation of 0.2-1.0% of an anionic phosphate ester mixture (monoalkyl:dialkyl weight ratios of 1:10 to 10:1) to reduce the grain formation in a sodium lauryl sulfate-calcium carbonate composition to produce a smooth paste. U.S. Pat. No. 4,350,680 asserts reduction in the sloughing or desquamation of oral mucosa during tooth brushing action if at least 0.2% of an anionic phosphate ester surface active agent is used as an additional surfactant to sodium lauryl sulfate. U.S. Pat. No. 5,019,373 asserts special advantages for the incorporation of shorter alkyl chain (C6 to C9) dialkyl phosphate esters, particularly dioctyl phosphate. The phosphate ester concentration at 2-4 wt. % in the dentifrice formulation. Evidence for anti-caries activity was offered, which showed a lower rate of calcium demineralization on teeth (in vitro) treated with 1% dioctyl phosphate solution compared to both a 1% sodium lauryl sulfate, which was similar to plain water (placebo), and 1 ppm sodium fluoride (the positive control).

SUMMARY OF THE INVENTION

The present inventions uses mono-, di-, and polyol phosphate esters (like PEG phosphate esters, PPG phosphate esters, glycerine phosphate esters) to provide multiple benefits to oral care formulations. The concentrations in which they may be used can vary depending on the intended purpose and the amount of benefit desired. These molecules with a hydrophilic nature are expected to assist in removing stains from teeth. They may also assist in preventing staining of teeth by being adsorbed onto teeth. The oral hygiene compositions of the invention include: providing an ablatable coating for anti-adherence of stain and bacteria to teeth; desensitization of teeth having dentinal hypersensitivity; low irritancy and improved tissue compatibility or tolerance; increased deposition of various ingredients, including antimicrobials, flavor oils; compatibility with peroxide whitening agents; and anti-tartar characteristics.

In a first aspect, the present invention is directed to an oral care composition, comprising:

(a) from about 10% to about 99% of at least one ingredient selected from the group consisting of a polishing agent (abrasive agent), sudsing agents (surfactants), a binder, a humectant, a medicinal agent, peroxide sources, alkali metal bicarbonate salts, thickening materials, water, titanium dioxide, flavor agents, sweetening agents, xylitol, coloring agents, water and mixtures thereof, and (b) an ionic hydrophyllizing agent comprising:
(b)(I) an organophosphorus material selected from:
   (b)(I)(1) organophosphorus compounds according to structure (I):

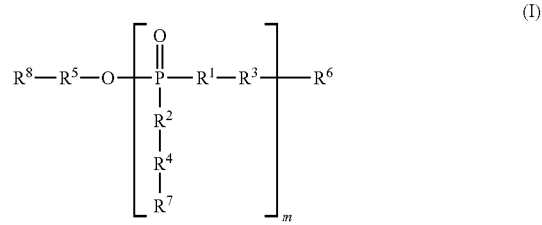

wherein:
each $R^1$ is and each $R^2$ is independently absent or O, provided that at least one of $R^1$ and $R^2$ is O, each $R^3$ is independently alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy, $R^5$ is and each $R^4$ is independently absent or alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy, $R^6$ and $R^8$ are each and each $R^7$ is independently H, or $(C_1-C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, or $-POR^9R^{10}$, $R^9$ and $R^{10}$ are each independently hydroxyl, alkoxy, aryloxy, or $(C_1-C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, and m is an integer of from 1 to 5, (b)(I)(2) salts of organophosphorus compounds according to structure (I), (b)(I)(3) condensation reaction products of two or more molecules of one or more organophosphorus compounds according to structure (I), and (b)(I)(4) mixtures comprising two or more of the compounds, salts, and/or reaction products of (b)(I)(1), (b)(I)(2), and (b)(I)(3), (b)(II) a vinyl alcohol material selected from:
(b)(II)(1) polymers comprising monomeric units according to structure (I-a):

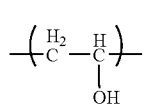

(b)(II)(2) salts of polymers (b)(II)(1),
(b)(II)(3) reaction products of two or more molecules of one or more polymers (b)(II)(1), and
(b)(II)(4) mixtures comprising two or more of the polymers, salts, and/or reaction products of (b)(II)(1), (b)(II)(2), and (b)(II)(3).

The invention further relates to the use of organophosphorus material in a dentifrice, particularly standard toothpaste.

The invention also relates to a tooth cleaning product comprising an organophosphorus material, an abrasive agent (polishing agent) and optionally a liquid.

The invention provides a mouthwash comprising:
(a) anti-staining agent comprising the organophosphorus material described herein;
(b) alcohol; and
(c) water.

Additionally, the longer term use of the organophosphorus material based dentifrice in accordance with the invention has an unexpectedly long lasting, beneficial therapeutic effect.

DETAILED DESCRIPTION OF THE INVENTION

Figure 1:
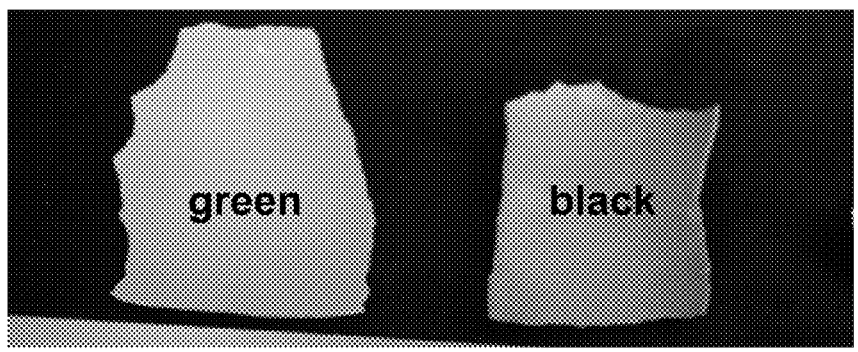
FIG. 1 shows a photograph of egg-shell brushed with commercial toothpaste, then stained with green (left) and black (right) tea, and then brushed again with commercial toothpaste.

As used herein, the terminology "hydrophobic surface" means a surface that exhibits a tendency to repel water and to thus resist being wetted by water, as evidenced by a water contact angle of greater than or equal to 70°, more typically greater than or equal to 90°, and/or a surface free energy of less than or equal to about 40 dynes/cm.

As used herein, the terminology "hydrophilic surface" means a surface that exhibits an affinity for water and to thus be wettable by water, as evidenced by a water contact angle of less than 70°, more typically less than 60° and/or a surface energy of greater than about 40 dynes/cm, more typically greater than or equal to about 50 dynes/cm.

As used herein in reference to a hydrophobic surface, the term "hydrophilizing" means rendering such surface more hydrophilic and thus less hydrophobic, as indicated by a decreased water contact angle. One indication of increased hydrophilicity of a treated hydrophobic surface is a decreased water contact angle with a treated surface compared to the water contact angle with an untreated surface.

A used herein in reference to a substrate, the terminology "water contact angle" means the contact angle exhibited by a droplet of water on the surface as measured by a conventional image analysis method, that is, by disposing a droplet of water on the surface, typically a substantially flat surface, at 25° C., photographing the droplet, and measuring the contact angle shown in the photographic image.

Surface energy is estimated using the Young equation:

$$\cos(\theta)^* \gamma_{lv} = \gamma_{sv} - \gamma_{sl}$$

with the contact angle θ, the interfacial energy $\gamma_{sv}$ between the solid and the vapor phase, the interfacial energy $\gamma_{sl}$ between the solid and the liquid phase, and the interfacial energy $\gamma_{lv}$ between the liquid and the vapor phase, and $\gamma_{sv}$ represents the surface energy of the solid.

As used herein, "molecular weight" in reference to a polymer or any portion thereof, means to the weight-average molecular weight ("$M_w$") of said polymer or portion, wherein $M_w$ of a polymer is a value measured by gel permeation chromatography and $M_w$ of a portion of a polymer is a value calculated according to known techniques from the amounts of monomers, polymers, initiators and/or transfer agents used to make the said portion.

As used herein, the notation "$(C_n-C_m)$" in reference to an organic group or compound, wherein n and m are integers, means that the group or compound contains from n to m carbon atoms per such group or compound.

The oral formulation of the present invention may be in the form of a toothpaste or dentifrice. The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. Each dentifrice composition will be contained in a physically separated compartment of a dispenser and dispensed side-by-side.

The term "oral formulation" as used herein means the total dentifrice delivered to the oral surfaces. The oral formulation is a combination of the two or more dentifrice compositions. The oral formulation is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the oral compositions of the present invention. Such materials include abrasive polishing materials, peroxide sources, alkali metal bicarbonate salts, thickening materials, humectants, water, surfactants, titanium dioxide, flavor system, sweetening agents, xylitol, coloring agents, and mixtures thereof.

The present compositions comprise essential components, as well as optional components. The essential and optional components of the compositions of the present invention are described in the following paragraphs.

Compositions for oral care include a wide variety of products, such as toothpastes, mouthwashes, and rinses.

Organophosphorus Material

The present invention includes oral care compositions comprising a surface active agent and a hydrophyilizing agent comprising organophosphorus material selected from:
(1) organophosphorus compounds according to structure (I):

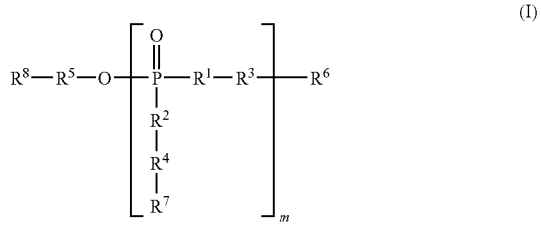

wherein:
each $R^1$ is and each $R^2$ is independently absent or O, provided that at least one of $R^1$ and $R^2$ is O,
each $R^3$ is independently alkyleneoxy, poly(alkyleneoxy), which may optionally, be substituted on one or more carbon atom of such alkyleneoxy, or poly (alkyleneoxy) group by hydroxyl, alkyl, hydroxyalkyl, alkoxy, alkenyl, aryl, or aryloxy,
$R^5$ is and each $R^4$ is independently absent or alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy,
$R^6$ and $R^8$ are each and each $R^7$ is independently H, or $(C_1$-$C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, or —$POR^9R^{10}$,
$R^9$ and $R^{10}$ are each independently hydroxyl, alkoxy, aryloxy, or $(C_1$-$C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, and
m is an integer of from 1 to 5,
(2) salts of organophosphorus compounds according to structure (I),
(3) condensation reaction products of two or more molecules of one or more organophosphorus compounds according to structure (I), and
(4) mixtures comprising two or more of the compounds, salts, and/or reaction products of (1), (2), and (3).

Suitable organophosphorus materials are also described in U.S. provisional patent application Nos. 60/842,265, filed Sep. 5, 2006 and 60/812,819, filed Jun. 12, 2006, both incorporated herein by reference.

As used herein, the term "alkyl" means a monovalent saturated straight chain or branched hydrocarbon radical, typically a monovalent saturated $(C_1$-$C_{30})$hydrocarbon radical, such as for example, methyl, ethyl, n-propyl, iso-propyl, n-butyl, sec-butyl, t-butyl, pentyl, or n-hexyl, which may optionally be substituted on one or more of the carbon atoms of the radical. In one embodiment, an alkyl radical is substituted on one or more carbon atoms of the radical with alkoxy, amino, halo, carboxy, or phosphono, such as, for example, hydroxymethyl hydroxyethyl, methoxymethyl, ethoxymethyl, isopropoxyethyl, aminomethyl, chloromethyl or trichloromethyl, carboxyethyl, or phosphonomethyl.

As used herein, the term "hydroxyalkyl" means an alkyl radical substituted on one of its carbon atoms with a hydroxyl group.

As used herein, the term "alkoxyl" means an oxy radical substituted with an alkyl group, such as for example, methoxyl, ethoxyl, propoxyl, isopropoxyl, or butoxyl, which may optionally be further substituted on one or more of the carbon atoms of the radical.

As used herein, the term "cycloalkyl" means a saturated cyclic hydrocarbon radical, typically a $(C_3$-$C_8)$ saturated cyclic hydrocarbon radical, such as, for example, cyclohexyl or cyclooctyl, which may optionally be substituted on one or more of the carbon atoms of the radical.

As used herein, the term "alkenyl" means an unsaturated straight chain, branched chain, or cyclic hydrocarbon radical that contains one or more carbon-carbon double bonds, such as, for example, ethenyl, 1-propenyl, or 2-propenyl, which may optionally be substituted on one or more of the carbon atoms of the radical. As used herein, the term "aryl" means a monovalent unsaturated hydrocarbon radical containing one or more six-membered carbon rings in which the unsaturation may be represented by three conjugated double bonds, such as for example, phenyl, naphthyl, anthryl, phenanthryl, or biphenyl, which may optionally be substituted one or more of carbons of the ring. In one embodiment, an aryl radical is substituted on one or more carbon atoms of the radical with hydroxyl, alkenyl, halo, haloalkyl, or amino, such as, for example, methylphenyl, dimethylphenyl, hydroxyphenyl, chlorophenyl, trichloromethylphenyl, or aminophenyl.

As used herein, the term "aryloxy" means an oxy radical that is substituted with an aryl group, such as for example, phenyloxy, methylphenyl oxy, isopropylmethylphenyloxy.

As used herein, the indication that a radical may be "optionally substituted" or "optionally further substituted" means, in general, unless further limited, either explicitly or by the context of such reference, that such radical may be substituted with one or more inorganic or organic substituent groups, such as, for example, alkyl, alkenyl, aryl, aralkyl, alkaryl, a hetero atom, or heterocyclyl, or with one or more functional groups that are capable of coordinating to metal ions, such as hydroxyl, carbonyl, carboxyl, amino, imino, amido, phosphonic acid, or sulphonic acid, or inorganic and organic esters thereof, such as, for example, sulphate or phosphate, or salts thereof.

As used herein, the terminology "$(C_x$-$C_y)$" in reference to an organic group, wherein x and y are each integers, indicates the group may contain from x carbon atoms to y carbon atoms per group.

In one embodiment, $R^6$ and $R^8$ are each and each $R^7$ is independently H, $(C_1$-$C_{30})$alkyl, $(C_1$-$C_{30})$alkenyl, or $(C_7$-$C_{30})$alkaryl.

In one embodiment, each $R^1$ and each $R^2$ is O, and the organophosphorus compound is selected from:

(II)(1) an organophosphate ester according to structure (II):

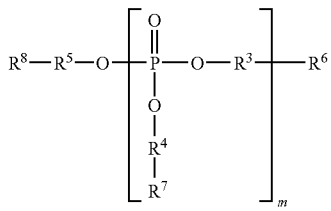

(II)

wherein $R^3$, $R^4$, $R^5$, $R^6$, $R^7$, $R^8$, and m are each as described above,
(II)(2) salts of organophosphorus compounds according to structure (II),
(II)(3) condensation reaction products of two or more molecules of one or more organophosphorus compounds according to structure (II), and
(II)(4) mixtures comprising two or more of the compounds, salts, and/or reaction products of (II)(1), (II)(2), and (II)(3).

In one embodiment, each $R^1$ is absent, each $R^2$ is O, and the organophosphorus compound is selected from:
(III)(1) an organophosphonate ester according to structure (III):

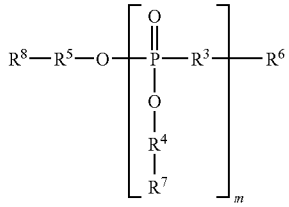

(III)

wherein $R^3$, $R^4$, $R^5$, $R^6$, $R^7$, $R^8$, and m are each as described above,
(III)(2) salts of organophosphorus compounds according to structure (III),
(III)(3) condensation reaction products of two or more molecules of one or more organophosphorus compounds according to structure (III), and
(III)(4) mixtures comprising two or more of the compounds, salts, and/or reaction products of (III)(1), (III)(2), and (III)(3).

In one embodiment, each $R^1$ is O, each $R^2$ is absent, and the organophosphorus compound is selected from:
(IV)(1) an organophosphonate ester according to structure (IV):

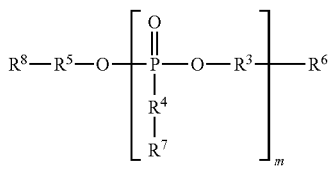

(IV)

wherein $R^3$, $R^4$, $R^5$, $R^6$, $R^7$, $R^8$, and m are each as described above, (IV)(2) salts of organophosphorus compounds according to structure (IV),
(IV)(3) condensation reaction products of two or more molecules of one or more organophosphorus compounds according to structure (IV), and
(IV)(4) mixtures comprising two or more of the compounds, salts, and/or reaction products of (IV)(1), (IV)(2), and (IV)(3).

In one embodiment, each $R^3$ is a divalent radical according to structure (V), (VI), (VII), or (VIII):

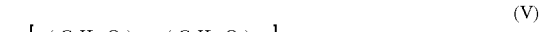

(V)

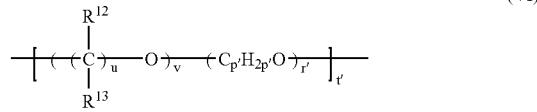

(VI)

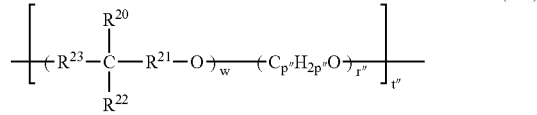

(VII)

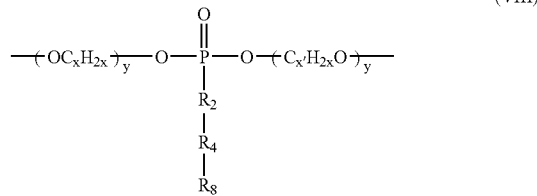

(VIII)

wherein:
each $R^{12}$ and each $R^{13}$ is independently H, hydroxyl, alkyl, hydroxyalkyl, alkoxy, alkenyl, aryl, aryloxy, or two $R^{12}$ groups that are attached to the adjacent carbon atoms may be fused to form, together with the carbon atoms to which they are attached, a $(C_6-C_8)$hydrocarbon ring,
$R^{20}$ is H, hydroxyl, alkyl, hydroxyalkyl, alkoxy, alkenyl, aryl, or aryloxy
$R^{22}$ is hydroxyl or hydroxyalkyl, provided that $R^{20}$ and $R^{22}$ are not each hydroxyl,
$R^{23}$ and $R^{21}$ are each independently methylene or poly(methylene),
p, p', p", q, and x are each independently integers of from 2 to 5,
each r, s, r', r", and y is independently a number of from 0 to 25,
provided that at least one of r and s is not 0,
u is an integer of from 2 to 10,
v and w are each numbers of from 1 to 25, and
t, t', and t" are each numbers of from 1 to 25, provided that the product of the quantity (r+s) multiplied times t is less than or equal to about 100, the product of the quantity (v+r') multiplied times t' is less than or equal to about 100, and the product of the quantity (w+r") multiplied time t" is less than or equal to about 100.

In one embodiment, each $R^4$ and each $R^5$ is independently absent or a divalent radical according to structure (V), (VI), or (VII), wherein $R^{12}$, $R^{13}$, $R^{20}$, $R^{21}$, $R^{22}$, $R^{23}$, p, p', p", q, r, r', r", s, t, t", t, u, v, w, x, and y are as described above.

In one embodiment, each $R^3$ is independently a divalent radical according to structure (V), (VI), or (VII) wherein $R^{12}$, $R^{13}$, $R^{20}$, $R^{21}$, $R^{22}$, $R^{23}$, p, p', p", q, r, r', r", s, t, t", t, u, v, w, x, and y are as described above, and $R^4$ and $R^5$ are each independently absent or $R^3$.

In one embodiment, each $R^3$ is independently a divalent radical according to structure (V), wherein p is 2, 3, or 4, r is an integer from 1 to 25, s is 0, t is an integer of from 1 to 2, and $R^4$ and $R^5$ are each independently absent or $R^3$.

In one embodiment, each $R^3$ is independently a divalent radical according to structure (VI), wherein the $R^{12}$ groups are fused to form, including the carbon atoms to which they are attached, a ($C_6$-$C_8$) hydrocarbon ring, each $R^{13}$ is H, p' is 2 or 3, u is 2, v is an integer of from 1 to 3, r' is an integer from 1 to 25, t' is an integer of from 1 to 25, the product of the quantity (v+r') multiplied times t" is less than or equal to about 100, more typically less than or equal to about 50, and $R^4$ and $R^5$ are each independently absent or $R^3$.

In one embodiment, each $R^3$ is independently a divalent radical according to structure (VII), wherein $R^{20}$ is hydroxyl or hydroxyalkyl, $R^{22}$ is H, alkyl, hydroxyl, or hydroxyalkyl, provided that $R^{20}$ and $R^{22}$ are not each hydroxyl, $R^{21}$ and $R^{23}$ are each independently methylene, di(methylene), or tri(methylene), w is 1 or 2, p" is 2 or 3, r" is an integer from 1 to 25, t" is an integer of from 1 to 25, the product of the quantity (w+r") multiplied times t" is less than or equal to about 100, more typically less than or equal to about 50, and $R^4$ and $R^5$ are each independently absent or $R^3$.

In one embodiment of the organophosphorus compound according to structure (II):
$R^6$ and $R^8$ are each and each $R^7$ is independently H or ($C_1$-$C_{30}$)hydrocarbon, which hydrocarbon may optionally be substituted on one or more carbon atoms by hydroxyl, fluorine, alkyl, alkenyl or aryl and/or interrupted at one or more sites by an O, N, or S heteroatom, or —$POR^9R^{10}$, more typically, $R^6$, $R^8$, and each $R^7$ are each H,
$R^4$ and $R^5$ are each absent,
each $R^3$ is independently a divalent radical according to structure (V), (VI), or (VII), and
m is an integer of from 1 to 5.

In one embodiment of the organophosphorus compound according to structure (II):
$R^6$, $R^8$, and each $R^7$ are each H,
$R^4$ and $R^5$ are each absent,
each $R^3$ is independently a divalent radical according to structure (V),
each p is independently 2, 3, or 4, more typically 2 or 3,
each r is independently a number of from 1 to about 100, more typically from
2 to about 50,
each s is 0,
each t is 1, and
m is an integer of from 1 to 5.

In one embodiment, the organophosphorus material is selected from:
(X)(1) organophosphorus compounds according to structure (IX):

(IX)(2) salts organophosphorus compounds according to structure (IX), and
(IX)(3) mixtures comprising two or more of the compounds and/or salts of (IX)(1) and (IX)(2).

In one embodiment of the organophosphorus compound according to structure (II):
$R^6$, $R^8$, and each $R^7$ are each H,
$R^4$ and $R^5$ are each absent,
each $R^3$ is independently a divalent radical according to structure (VI),
the $R^{12}$ groups are fused to form, including the carbon atoms to which they are attached, a ($C_6$-$C_8$)hydrocarbon ring,
each $R^{13}$ is H
p' is 2 or 3,
u is 2,
v is 1,
r' is a number of from 1 to 25,
t' is a number of from 1 to 25,
the product of the quantity (v+r') multiplied times t' is less than or equal to about 100, and
m is an integer of from 1 to 5.

In one embodiment of the organophosphorus compound according to structure (II):
$R^6$, $R^8$, and each $R^7$ are each H,
$R^4$ and $R^5$ are each absent,
each $R^3$ is independently a divalent radical according to structure (VII),
$R^{20}$ is hydroxyl or hydroxyalkyl,
$R^{22}$ is H, alkyl, hydroxyl, or hydroxyalkyl,
$R^{23}$ and $R^{21}$ are each independently methylene, di(methylene), or tri(methylene),
w is 1 or 2,
p" is 2 or 3,
r" is a number of from 1 to 25,
t" is a number of from 1 to 25
the product of the quantity (w+r") multiplied times t" is less than or equal to about 100, and
m is an integer of from 1 to 5.

In one embodiment, the organophosphorus compound is according to structure (III), each $R^3$ is a divalent radical according to structure (V) with s=0 and t=1, $R^4$ and $R^5$ are each absent, and $R^6$, $R^7$, and $R^8$ are each H.

In one embodiment, the organophosphorus compound is according to structure (IV), wherein R3 and R5 are each according to structure (V), with s=0 and t=1, and $R^6$ and $R^8$ are each H.

In one embodiment, the organophosphorus material (b)(I) comprises a condensation reaction product of two or more molecules according to structure (I).

In one embodiment, the organophosphorus material (b)(I) comprises a condensation reaction product of two or more molecules according to structure (I) in the form of a linear molecule, such as, for example, a linear condensation reaction product according to structure (X), formed by condensation of a molecule according to structure (II) with a molecule according to structure (IV):

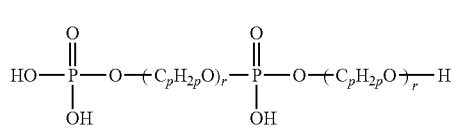

(IX)

wherein:
p is 2, 3, or 4, more typically 2 or 3,
r is a number of from 4 to about 50,

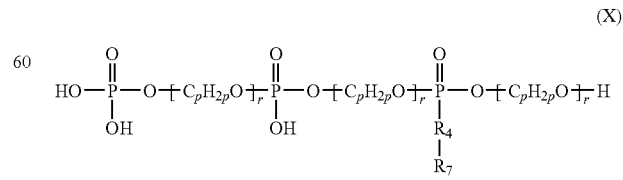

(X)

wherein $R^4$, $R^7$, p, r are each as described above.

In one embodiment, the organophosphorus material (b)(I) comprises a condensation reaction product of two or more molecules according to structure (I) in the form of a crosslinked network. A portion of an exemplary crosslinked condensation reaction product network is illustrated by structure (XI):

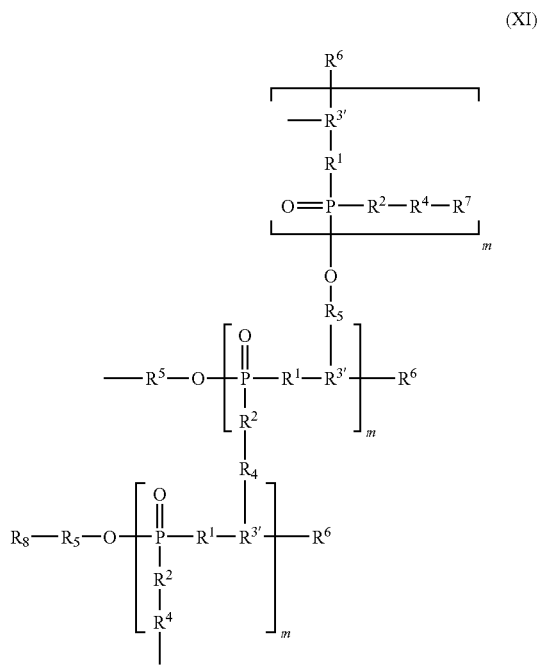

wherein $R^1$, $R^2$, $R^4$, $R^5$, $R^6$, $R^7$, $R^8$, and m are each as described above, and each $R^{3'}$ is independently a residue of an $R^3$ group of a compound according to structure (I), as described above, wherein the $R^3$ group is a alkyleneoxy or poly(alkyleneoxy) moiety substituted with hydroxyl-, hydroxyalkyl-, hydroxyalkyleneoxy- or hydroxypoly(alkyleneoxy)- on one or more carbon atoms of the alkyleneoxy or poly(alkyleneoxy) moiety, and —$R^{3'}$—$R_4$— and —$R^{3'}$—$R^5$— each represent a respective linkage formed by condensation of such an $R^3$ group and a —$R^{3'}$—$R^5$— or $R^8$—$R^5$— group of molecules of another molecule of a compound according to structure (I).

In one embodiment, the organophosphorus material (b)(I) comprises a condensation reaction product of two or more molecules according to structure (I) and the condensation reaction product forms a covalently crosslinked organophosphorus network. Typically the solubility of the covalently crosslinked organophosphorus network in water is less than that of the organophosphorus compound according to structure (I), more typically, the covalently crosslinked organophosphorus network is substantially insoluble in water.

As used herein, the term "salts" refers to salts prepared from bases or acids including inorganic or organic bases and inorganic or organic acids.

In one embodiment, the organophosphorus material (b)(I) is in the form of a salt that comprises an anion derived (for example, by deprotonation of a hydroxyl or a hydroxyalkyl substituent) from an organophosphorus compound according to structure (I) and one or more positively charged counterions derived from a base.

Suitable positively charged counterions include inorganic cations and organic cations, such as for example, sodium cations, potassium cations, calcium cations, magnesium cations, copper cations, zinc cations, ammonium cations, tetraalkylammonium cations, as well as cations derived from primary, secondary, and tertiary amines, and substituted amines.

In one embodiment, the cation is a monovalent cation, such as for example, $Na^+$, or $K^+$.

In one embodiment, the cation is a polyvalent cation, such as, for example, $Ca^{+2}$, $Mg^{+2}$, $Zn^{+2}$, $Mn^{+2}$, $Cu^{+2}$, $Al^{+3}$, $Fe^{+2}$, $Fe^{+3}$, $Ti^{+4}$, $Zr^{+4}$, in which case the organophosphorus compound may be in the form of a "salt complex" formed by the organophosphorus compound and the polyvalent cation. For organophosphorus compound having two or more anionic sites, e.g., deprotonated hydroxyl substituents, per molecule, the organophosphorus compound-polyvalent cation complex can develop an ionically crosslinked network structure. Typically the solubility of the ionically crosslinked organophosphorus network in water is less than that of the organophosphorus compound according to structure (I), more typically, the ionically crosslinked organophosphorus network is substantially insoluble in water.

Suitable organophosphorus compounds can be made by known synthetic methods, such as by reaction of one or more compounds, each having two or more hydroxyl groups per molecule, with phosphoric acid, polyphosphoric acid, and or phosphoric anhydride, such as disclosed, for example, in U.S. Pat. Nos. 5,550,274, 5,554,781, and 6,136,221.

In one embodiment, cations are immobilized on a water insoluble substrate to form a water insoluble cationic particle and the hydophilizing layer further comprises cationic particles. Suitable substrates include inorganic oxide particles, including for example, oxides of single elements, such as cerium oxide, titanium oxide, zirconium oxide, halfnium oxide, tantalum oxide, tungsten oxide, silicon dioxide, and bismuth oxide, zinc oxide, indium oxide, and tin oxide, and mixtures of such oxides, as well as oxides of mixtures of such elements, such as cerium-zirconium oxides. Such particle may exhibit a mean particle diameter ("$D_{50}$") of from about 1 nanometer ("nm") to about 50 micrometers ("μm"), more typically from about 5 to about 1000 nm, even more typically from about 10 to about 800 nm, and still more typically from about 20 to about 500 nm, as determined by dynamic light scattering or optical microscopy. In one embodiment, aluminum cations are immobilized on silica particles.

Vinyl Alcohol Material

In one embodiment, the oral care product comprises a vinyl alcohol material (b)(II) as a hydrophilizing material.

In one embodiment, which offers improved solubility in water and improved processability, the vinyl alcohol material (b)(II) comprises a polymer that comprises monomeric units according to structure (I-a) (a "vinyl alcohol polymer").

In one embodiment, the vinyl alcohol polymer and exhibits a weight average molecular weight of greater than or equal to about 10,000, more typically from about 10,000 to about 100,000, even more typically from about 10,000 to about 30,000. In an alternative embodiment, which offers improved durability, the vinyl alcohol polymer a weight average molecular weight of greater than or equal to about 100,000, more typically form about 100,000 to about 200,000. In another embodiment, which offers a balance between processability and durability, the vinyl alcohol polymer exhibits a weight average molecular weight of greater than or equal to about 50,000, more typically from about 50,000 to about 150,000, even more typically from about 80,000 to about 120,000.

In one embodiment, the vinyl alcohol polymer is made by polymerizing a vinyl ester monomer, such as for example, vinyl acetate, to form a polymer, such as a poly(vinyl acetate) homopolymer or a copolymer comprising monomeric units derived from vinyl acetate, having a hydrocarbon backbone and ester substituent groups, and then hydrolyzing at least a portion of the ester substituent groups of the polymer to form hydroxy-substituted monomeric units according to structure (I-a). In one embodiment, which offers improved solubility in water and improved processability, the vinyl alcohol polymer exhibits a degree of hydrolysis of greater than or equal to about 88%, more typically from about 88% to about 95%. As used herein in reference to a vinyl alcohol polymer that is made by hydrolyzing a polymer initially having a hydrocarbon backbone and ester substituent groups, the term "degree of hydrolysis" means the relative amount, expressed as a percentage, of vinyl ester-substituted monomeric units that were hydrolyzed to form hydroxy-substituted monomeric units. In another embodiment, which offers improved solubility in water and improved durability, the vinyl alcohol polymer exhibits a degree of hydrolysis of greater than or equal to about 99%. In yet another embodiment, which offers a compromise between solubility in water and durability, the polymer exhibits a degree of hydrolysis from about 92 to about 99%.

In one embodiment, the vinyl alcohol polymer has a linear polymeric structure. In an alternative embodiment, the vinyl alcohol polymer has a branched polymeric structure.

In one embodiment, the vinyl alcohol polymer is a vinyl alcohol homopolymer that consists solely of monomeric units according to structure (I-a).

In one embodiment, the vinyl alcohol polymer is a vinyl alcohol copolymer that comprises monomeric units having a structure according to structure (I-a) and further comprises comonomeric units having a structure other than structure (I-a). In one embodiment, the vinyl alcohol polymer is a copolymer that comprises hydroxy-substituted monomeric units according to (I-a) and ester substituted monomeric units and is made by incomplete hydrolysis of a vinyl ester homopolymer.

In one embodiment a vinyl alcohol copolymer comprises greater than or equal to about 50 mole % ("mol %"), more typically greater or equal to than about 80 mol %, monomeric units according to structure (I-a) and less than about 50 mol %, more typically less than about 20 mol %, comonomeric units having a structure other than structure (I-a).

As described above, vinyl alcohol polymers having monomeric units according to structure (I-a) are typically derived from polymerization of vinyl ester monomers and subsequent hydrolysis of vinyl ester-substituted monomeric units of the polymer. Suitable vinyl alcohol copolymers are typically derived by copolymerization of the vinyl ester monomer with any ethylenically unsaturated monomer that is copolymerizable with the vinyl ester monomer, including for example, other vinyl monomers, allyl monomers, acrylic acid, methacrylic acid, acrylic ester monomers, methacrylic ester monomers, acrylamide monomers, and subsequent hydrolysis of at least a portion of the ester-substituted monomeric units to form hydroxy-substituted monomeric units according to structure (I-a).

In one embodiment, the vinyl alcohol polymer comprises monomeric units according to structure (I-a) and further comprises hydrophilic monomeric units other than the monomeric according to structure (I-a). As used herein, the term "hydrophilic monomeric units" are those wherein homopolymers of such monomeric units are soluble in water at 25° C. at a concentration of 1 wt % homopolymer, and include, for example, monomeric units derived from, for example, hydroxy($C_1$-$C_4$)alkyl(meth)acrylates, (meth)acrylamide, ($C_1$-$C_4$)alkyl(meth)acrylamides, N,N-dialkyl-acrylamides, alkoxylated(meth)acrylates, poly(ethylene glycol)-mono methacrylates and poly(ethyleneglycol)-monomethylether methacrylates, hydroxy($C_1$-$C_4$)acrylamides and methacrylamides, hydroxyl($C_1$-$C_4$)alkyl vinyl ethers, N-vinylpyrrole, N-vinyl-2-pyrrolidone, 2- and 4-vinylpyridine, ethylenically unsaturated carboxylic acids having a total of 3 to 5 carbon atoms, amino($C_1$-$C_4$)alkyl, mono($C_1$-$C_4$)alkylamino($C_1$-$C_4$) alkyl, and di($C_1$-$C_4$)alkylamino($C_1$-$C_4$)alkyl (meth)acrylates, allyl alcohol, dimethylaminoethyl methacrylate, dimethylaminoethylmethacrylamide.

In one embodiment, the vinyl alcohol polymer comprises monomeric units according to structure (I-a) and further comprises hydrophobic monomeric units. As used herein, the term "hydrophobic monomeric units" are those wherein homopolymers of such monomeric units are insoluble in water at 25° C. at a concentration of 1 wt % homopolymer, and include, for example, monomeric units derived from ($C_1$-$C_{18}$)alkyl and ($C_5$-$C_{18}$)cycloalkyl (meth)acrylates, ($C_5$-$C_{18}$) alkyl(meth)acrylamides, (meth)acrylonitrile, vinyl ($C_1$-$C_{18}$) alkanoates, ($C_2$-$C_{18}$)alkenes, ($C_2$-$C_{18}$)haloalkenes, styrene, ($C^1$-$C_6$)alkylstyrenes, ($C_4$-$C_{12}$)alkyl vinyl ethers, fluorinated ($C_2$-$C_{10}$)alkyl (meth)acrylates, ($C_3$-$C_{12}$)perfluoroalkylethylthiocarbonylaminoethyl(meth)acrylates, (meth)acryloxyalkylsiloxanes, N-vinylcarbazole, ($C_1$-$C_{12}$) alkyl maleic, fumaric, itaconic, and mesaconic acid esters, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate, and 3-methacryloxypropylpentamethyldisiloxane.

As used herein, the term "(meth)acrylate" means acrylate, methacrylate, or acrylate and methacrylate and the term (meth)acrylamide" means acrylamide, methacrylamide or acrylamide and methacrylamide.

In one embodiment, the polymer comprising monomeric units according to structure (I-a) a random copolymer. In another embodiment, the copolymer comprising monomeric units according to structure (I-a) is a block copolymer.

Methods for making suitable vinyl alcohol polymers are known in the art. In one embodiment, a polymer comprising monomeric units according to structure (I-a) is made by polymerizing one or more ethylenically unsaturated monomers, comprising at least one vinyl ester monomer, such vinyl acetate, by known free radical polymerization processes and subsequently hydrolyzing at least a portion of the vinyl ester monomeric units of the polymer to make a polymer having the desired degree of hydrolysis. In another embodiment, the polymer comprising monomeric units according to structure (I-a) is a copolymer made by known controlled free radical polymerization techniques, such as reversible addition fragmentation transfer (RAFT), macromolecular design via interchange of xanthates (MADIX), or atom transfer reversible polymerization (ATRP).

In one embodiment, the vinyl alcohol polymer is made by known solution polymerization techniques, typically in an aliphatic alcohol reaction medium.

In another embodiment, the vinyl alcohol polymer is made by known emulsion polymerization techniques, in the presence of one or more surfactants, in an aqueous reaction medium.

In one embodiment, the vinyl alcohol material comprises a microgel made by crosslinking molecules of a vinyl alcohol polymer.

In one embodiment the vinyl alcohol material comprises a salt, such as a sodium or potassium salt, of a vinyl alcohol polymer.

Compositions

The organophosphorus material described herein may also be used in a variety of oral care products. The composition according to the invention can be provided in any form and can be used in multiple ways. Thus, it can be in the form of a paste, gel or liquid. For example, the organophosphorus material may be used in toothpastes (as described by U.S. Pat. No. 5,939,052), and mouth detergents (as described by U.S. Pat. No. 6,767,560), and other dentifrices (as described by U.S. Patent Application Publication No. 2004/0185207). Each of the documents discussed in this paragraph are expressly incorporated by reference in their entireties.

A toothpaste or gel in accordance with the invention will generally comprise an organophosphorus material as described above, a surfactant agent, a compatible abrasive agent system, and a liquid in an amount to provide the desired consistency.

In an exemplary toothpaste, the liquid may include water, humectant and binder, generally, in an amount ranging from about 10 to about 90% by weight of the toothpaste. Water is a desirable component when a toothpaste or gel is being prepared. Water comprises up to about 50%, and preferably about 5-35% by weight of the toothpaste. However, an anhydrous toothpaste or gel can be formulated if desired.

A tooth powder in accordance with the invention may comprise a polishing agent which is compatible with the soluble monoalkyl and dialkyl phosphate ester salts described herein, such as sodium bicarbonate or hydrated silica. Generally, the polishing agent will be in an amount from about 20 to about 95%, and preferably above 50% by weight of the formulation. An effective amount of the monoalkyl and dialkyl phosphate esters as described herein is typically from about 0.1 to about 10% and preferably about 1% to about 5% by weight of the tooth powder formulation. Optional, but preferred, components which may be included in the toothpowder are a flavoring agent and/or sweetening agent, an anti-calculus agent such as a water-soluble alkali metal salt of a polyphosphate, an anti-caries agent such as sodium fluoride or sodium monofluorophosphate, buffering agents such as alkali metal orthophosphates, phosphoric acid, alkali metal glycerophosphates, tartrates, or citrates, and one or more processing aids such as a flow aid to insure product uniformity.

A mouthwash in accordance with the invention generally comprises alcohol, water, humectant, and optionally an effective amount of the monoalkyl and dialkyl phosphate ester salts as described herein. An effective amount of the monoalkyl and dialkyl phosphate ester salts in the mouthwash is typically from about 0.1% to about 10% and preferably from about 1% to about 5% by weight of the mouthwash. Optional, but preferred, components which are included in the mouthwash are a flavoring agent and/or sweetening agent, an anti-calculus agent such as a water-soluble alkali metal salt of a polyphosphate, an anti-caries agent such as sodium fluoride or sodium monofluorophosphate, buffering agents such as alkali metal orthophosphates, phosphoric acid, alkali metal glycerophosphates, tartrates, or citrates.

As used herein, terms "aqueous medium" and "aqueous media" are used herein to refer to any liquid medium of which water is a major component. Thus, the term includes water per se as well as aqueous solutions and dispersions. For example, the aqueous medium may be a liquid bodily discharge, such as urine, menses, and saliva.

In one embodiment, the oral care composition comprises, based on 100 parts by weight ("pbw") of the composition, from about 0.1 to about 20 pbw, more typically, from about 1 to about 5 pbw, organophosphorus material, and from about 80 to 99 pbw, more typically, from about 90 to about 98 pbw, carrier.

The pH of the composition or the pH of use of the composition according to the invention can vary, depending on the application. The pH of the compositions is not critical and can be in the range of from about 2 to about 12, preferably from about 4 to about 10 and most preferably from about 6 to about 8. The pH can be adjusted using a buffer such as citric acid.

The oral care composition of the invention can comprise, depending on its application, from 0.001 to 10% of its weight of at least one of the organophosphorus materials (phosphate esters).

The composition can be employed in an amount such that, after optional rinsing, the amount of phosphate esters deposited on the tooth surface is typically from 0.0001 to 10 mg/m$^2$, for example, 0.001 to 5 mg/m$^2$, of surface treated.

Unless otherwise indicated, when molar mass is referred to, the reference will be to the weight-average molar mass, expressed in g/mol. The latter can be determined by aqueous gel permeation chromatography (GPC) or by light scattering (DLS or alternatively MALLS), with an aqueous eluent or an organic eluent (for example dimethylacetamide, dimethylformamide, and the like), depending on the composition of the polymer.

Additional Ingredients

In addition to the organophosphorus material of the present invention, oral care products, such as mouthwashes, chewing gum, soluble oral care strips (similar to the LISTERINE® oral care strips), lozenges and toothpastes, of the present invention contain adjunct ingredients. Additional background on such products is provided by PCT application serial number PCT/US98/04474, filed Mar. 6, 1998 and published as WO 98/38973, as well as by U.S. Pat. No. 6,864,314, each of which is incorporated herein by reference in its entirety.

An oral hygiene composition in accordance with the invention may comprise, without intended limitation, components customarily used in this field, such as a polishing agent (abrasive agent), sudsing agents (surfactants), a binder, a humectant, a medicinal agent, peroxide sources, alkali metal bicarbonate salts, thickening materials, water, titanium dioxide, flavor agents, sweetening agents, xylitol, coloring agents, water and mixtures thereof. A popular, commercial anti-sensitivity agent is potassium nitrate. In preparing the present oral care compositions, it is desirable to add one or more of these additional ingredients to the compositions. Such materials are well known in the art and are readily chosen by one skilled in the art based on the physical and aesthetic properties desired for the compositions being prepared. These additional ingredients typically comprise from about 40% to about 99%, preferably from about 70% to about 98%, and more preferably from about 90% to about 95%, by weight of the dentifrice composition.

For example, optional, but preferred, components which may be included in oral care products in accordance with the invention are organic binders; inorganic thickeners, such as silica; secondary surfactants and/or sweetening agents; coloring agents and/or pigments; anti-microbial agents; and like components conventionally added to toothpastes and gels. Binders suitable for use in a composition of the invention include hydroxyethyl cellulose, and hydroxypropyl cellulose, as well as xanthan gums, Iris moss and gum tragacanth. Binders may be present in the amount from 0.01 to 10%. Sweeteners suitable for use, e.g. saccharin, may be present at levels of about 0.1% to 5%.

Abrasive Polishing Materials

An abrasive polishing material may also be included in the toothpaste compositions. The abrasive polishing material contemplated for use in the compositions of the present invention can be any material which does not excessively abrade dentin. Typical abrasive polishing materials include silicas including gels and precipitates; aluminas; phosphates including inorganic orthophosphates, pyrophosphates, metaphosphates, polyphosphates and hexametaphosphate salts; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Tuber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. Silica abrasives described in U.S. patent application Ser. Nos. 08/434,147 and 08/434,149, both filed May 2, 1995, are also herein incorporated by reference. The abrasive in the toothpaste compositions described herein is generally present at a level of from about 6% to about 70% by weight of the composition. Preferably, toothpastes contain from about 10% to about 50% of abrasive, by weight of the dentifrice composition.

Humectants

A humectant is also a desirable component in an oral care product, for example, toothpaste or gel. The humectant generally comprises from about 0% to 85%, and preferably from about 15% to 55%, by weight of the oral care composition. Preferably for toothpaste or gel, the humectant comprises about 5% to about 85% by weight of the formulation, and preferably from about 10% to about 70% by weight of the formulation. In translucent gels, where the refractive index is an important consideration, it is preferred to use higher ratios of humectant to water than in opaque pastes. For a gel the ratio of humectant to water should preferably be above about 0.5 to 1, and more preferably above 1 to 1.

Humectants contemplated for use in a composition of the invention include polyols, such as glycerol, sorbitol, polyethylene glycols, propylene glycol, hydrogenated partially hydrolyzed polysaccharides and the like. Exemplary amounts are provided below with reference to various types of compositions.

The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols.

Anti-caries Agent

Anti-caries agents may also be used in conjunction with the composition in accordance with the invention. Thus, the oral care composition of the present invention can incorporate a soluble fluoride source capable of providing free fluoride ions. For example oral hygiene compositions in accordance with the invention may include those commonly used in oral health care compositions, such as sodium fluoride, stannous fluoride, indium fluoride, sodium monofluorophosphate, zinc ammonium fluoride, tin ammonium fluoride, calcium fluoride and cobalt ammonium fluoride and the like. The present compositions contain a soluble fluoride ion source capable of providing from about 50 ppm to about 3500 ppm, and preferably from about 500 ppm to about 3000 ppm of free fluoride ions. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

Dyes/Colorants

Dyes/colorants suitable for oral health care compositions, i.e. FD & C Blue #1, FD & C Yellow #10, FD & C Red #40, etc., may be included as well. Various other optional ingredients may also be included in the compositions of the invention such as preservatives; vitamins, for example, vitamins C and E; and other anti-plaque agents, for example, stannous salts, copper salts, strontium salts and magnesium salts. Compositions may also include anti-calculus agents such as a water-soluble alkali metal salt of a polyphosphate, buffering agents such as alkali metal orthophosphates, phosphoric acid, alkali metal glycerophosphates, tartrates, or citrates, other anti-caries agents, for example, calcium glycerophosphate, sodium trimetaphosphate; anti-staining compounds, for example silicone polymers; plant extracts; and mixtures thereof. Additionally, polymers, particularly anionic polymers, such as polycarboxylates or polysulfonates, or polymers containing both a carboxylate and a sulfonate moiety, or phosphonate polymers may be used.

Buffering Agents

The present compositions each may contain a buffering agent. Buffering agents, as used herein, refer to agents that can be used to adjust the pH of the compositions to a range of about pH 6.5 to about pH 10. These agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Inorganic pyrophosphate salts are also suitable buffering agents. The pyrophosphate salts include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on the pH of the composition.

Compositions comprising predominately undissolved inorganic pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. Some or all of the tetrasodium pyrophosphate may be undissolved in the product and present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The pyrophosphate salts are described in more detail in Kirk & Othmer, Encyclopedia of Chemical Technology, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, U.S. Pat. No. 4,627,977, to Gaffar et al., the disclosure of which is incorporated herein by reference in its entirety; as well as, e.g., polyamino propoane sulfonic acid (AMPS), zinc citrate trihydrate, diphosphonates (e.g., EHDP; AHP), polypeptides (such as polyaspartic and polyglutamic acids), and mixtures thereof.

Thickening Agents

The present invention compositions in the form of toothpastes typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.1% to about 15%, by weight of the dentifrice composition.

Water

Water employed in the preparation of commercially suitable oral compositions should preferably be of low ion content and free of organic impurities. Water can generally comprise from about 5% to about 70%, and preferably from about 10% to about 50%, by weight of the composition herein. The amounts of water include the free water which is added plus that which is introduced with other materials, such as with sorbitol, silica, surfactant solutions, and/or color solutions.

Peroxide

The present invention may include a peroxide source in the composition. The peroxide source can be selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Sudsing Agents

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name TWEENS), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Colorants

Titanium dioxide may also be added to the present composition. Titanium dioxide is a white powder which adds opacity to the compositions. Titanium dioxide generally comprises from about 0.25% to about 5%, by weight of the composition.

Other coloring agents may also be added to the present composition. The coloring agent may be in the form of an aqueous solution, preferably 1% coloring agent in a solution of water. Color solutions generally comprise from about 0.01% to about 5%, by weight of the composition.

Dyes/colorants suitable for oral health care compositions, i.e. FD & C Blue #1, FD & C Yellow #10, FD & C Red #40, etc., may be included as well. Various other optional ingredients may also be included in the compositions of the invention such as preservatives; vitamins, for example, vitamins C and E; and other anti-plaque agents, for example, stannous salts, copper salts, strontium salts and magnesium salts. Compositions may also include anti-calculus agents such as a water-soluble alkali metal salt of a polyphosphate, buffering agents such as alkali metal orthophosphates, phosphoric acid, alkali metal glycerophosphates, tartrates, or citrates, other anti-caries agents, for example, calcium glycerophosphate, sodium trimetaphosphate; anti-staining compounds, for example silicone polymers; plant extracts; and mixtures thereof. Additionally, polymers, particularly anionic polymers, such as polycarboxylates or polysulfonates, or polymers containing both a carboxylate and a sulfonate moiety, or phosphonate polymers may be used.

Flavor and Sweetening Agents

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Other sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

Antibacterial and Antimicrobial Agents

The present invention may also include other agents, such as antibacterial agents and antimicrobial agents. Suitable antibacterial agents include phenolics and salicylamides.

Also, included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, copper glysinate, zinc citrate, and zinc lactate may also be included.

Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. The water insoluble antimicrobial agents, water soluble agents, and enzymes may be present in the composition. The quaternary ammonium agents, stannous salts, and substituted guanidines are preferably present in the second dentifrice composition. These agents may be present at levels of from about 0.01% to about 1.5%, by weight of the dentifrice composition.

To further illustrate the invention and the advantages thereof, the following non-limiting examples are given.

EXAMPLE 1

Egg Shell Tests

In this example egg-shell (as a substitute for teeth) was stained with green/black tea stain.

FIG. 1 shows a photograph of egg-shell brushed with commercial toothpaste, then stained with green (left) and black (right) tea, and then brushed again with commercial toothpaste. This resulted in no removal of tea stain.

Figure 2:
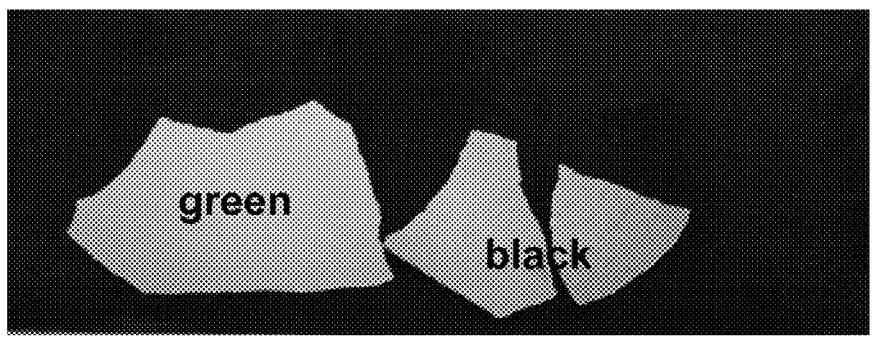
FIG. 2 shows a photograph of egg-shell brushed with commercial toothpaste plus 20% PEG400 phosphate ester (polyethylene glycol 400 phosphate ester), then stained with green (left) and black (right) tea, and then brushed again with toothpaste plus 20% PEG400 phosphate ester.

In another experiment PEG400 phosphate ester (a polyethylene glycol phosphate ester) was mixed directly into the toothpaste without neutralization. Egg-shell was brushed with commercial toothpaste plus 20% PEG400 phosphate ester, then stained with green and black tea, and then brushed again with commercial tooth-paste plus 20% PEG400 phosphate ester. FIG. 2 shows a photograph of the egg-shell brushed with the commercial toothpaste plus 20% PEG400 phosphate ester, then stained with green (left) and black (right) tea, and then brushed again with commercial toothpaste plus 20% PEG400 phosphate ester. This resulted in good removal of tea stain.

Figure 3:
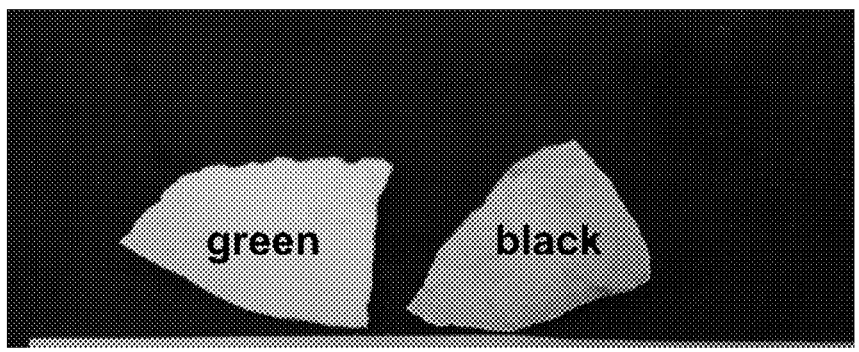
FIG. 3 shows a photograph of egg-shell brushed with commercial toothpaste plus 20% SDS, then stained with green (left) and black (right) tea, and then brushed with commercial toothpaste plus 20% SDS.

In another experiment 20% sodium dodecyl sulphate (SDS) was mixed into the commercial toothpaste. The 20% SDS was used as a 100% powder. FIG. 3 shows a photograph of egg-shell brushed with the commercial toothpaste plus 20% SDS, then stained with green (left) and black (right) tea, and then brushed with commercial toothpaste plus 20% SDS. This resulted in no/slight removal of tea stain.

Figure 4:
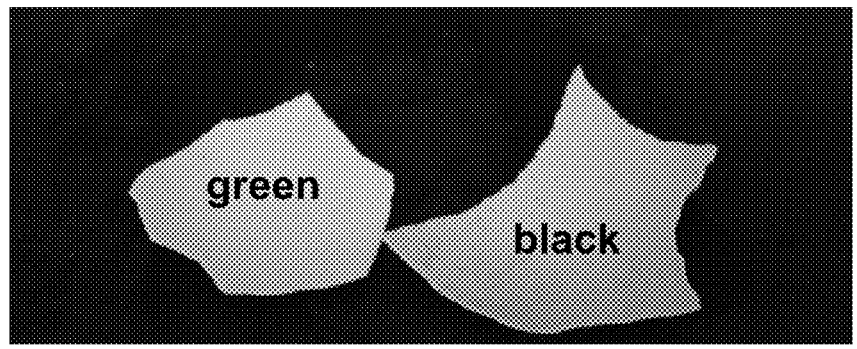
FIG. 4 shows a photograph of egg-shell brushed with commercial toothpaste plus 20% PEG1000 phosphate ester, then stained with green (left) and black (right) tea, and then brushed again with commercial toothpaste plus 20% P1000 phosphate ester.

In another experiment PEG1000 phosphate ester (a polyethylene glycol phosphate ester) was mixed directly into the toothpaste without neutralization. FIG. 4 shows a photograph of egg-shell brushed with the commercial toothpaste plus 20% PEG1000 phosphate ester, then stained with green (left) and black (right) tea, and then brushed again with commercial toothpaste plus 20% PEG1000 phosphate ester. This resulted in good removal of tea stain.

In a separate test it was noted that treatment of egg-shell with SDS or PEG phosphate ester, then staining and then simple rinsing does not improve removal of stain compared to untreated egg-shell. This implies improved cleaning is not due to creation of anti-soiling layer, but due to better cleaning capability.

EXAMPLE 2

Figure 5:
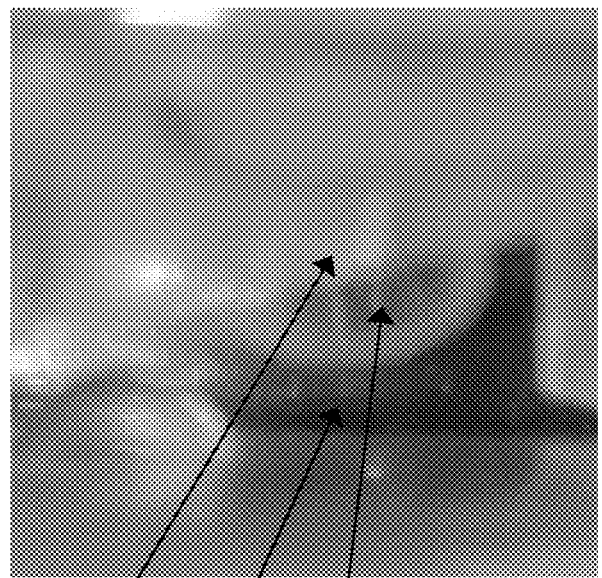
FIG. 5 shows a droplet of hexadecane under pure deionized water on CaCO3 crystal.

FIG. 5 shows a droplet of hexadecane under pure deionized water on CaCO3 crystal (as an additional substitute for teeth).

Figure 7:
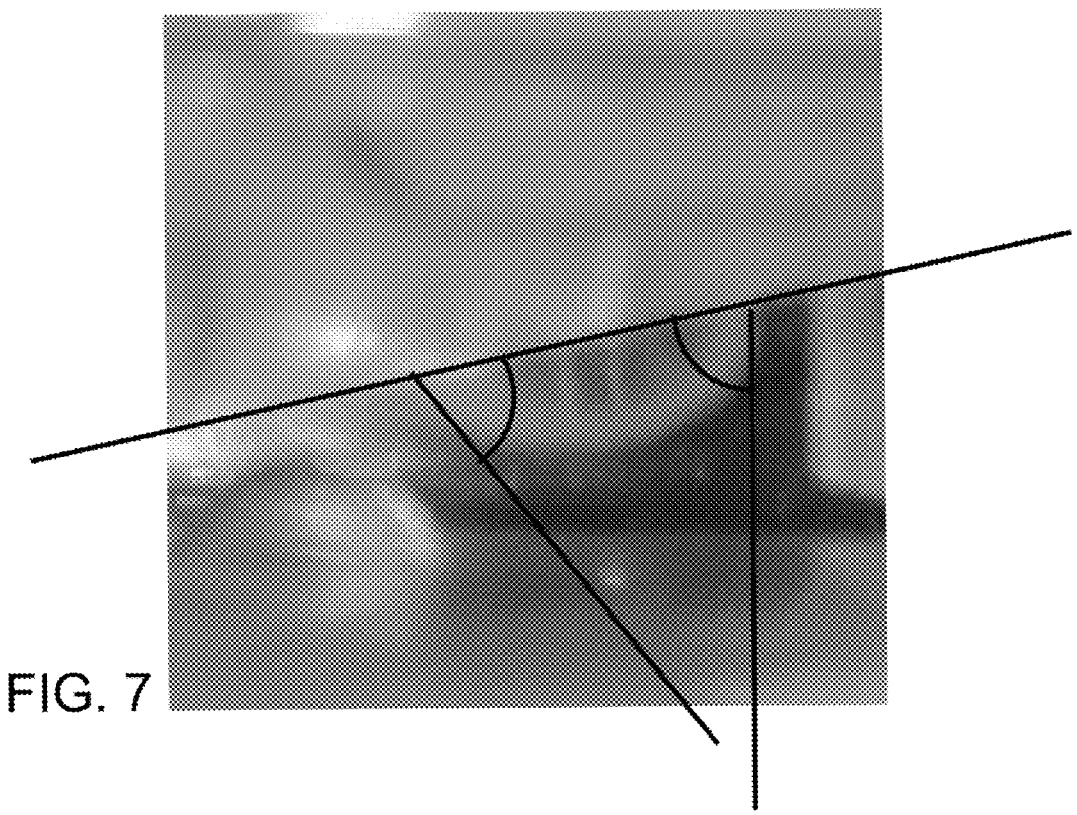
FIG. 7 is FIG. 5 labeled to show the contact angle.

FIG. 7 is FIG. 5 labeled to show the contact angle. FIG. 7 shows the contact angle was 60°-80°.

Figure 6:
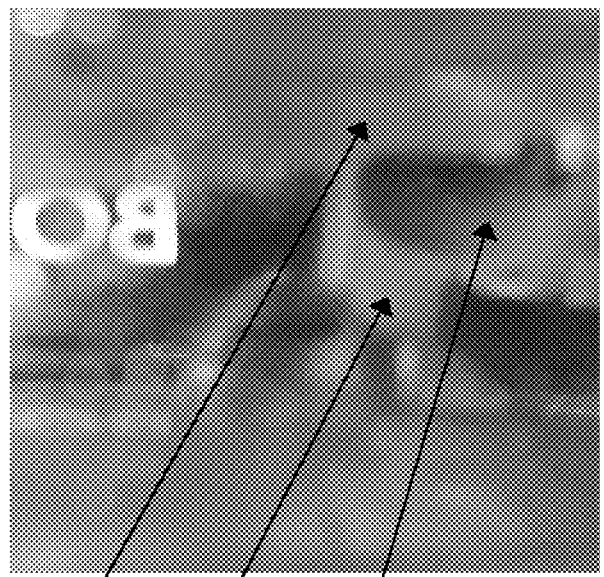
FIG. 6 shows a droplet of hexadecane under 1 wt. % PEG 1000 phosphate ester on CaCO3 crystal pretreated with PEG1000 phosphate ester to show the adsorption of PEG1000 phosphate ester onto the CaCO3 crystal increases the contact angle of hexadecane on CaCO3 under water.
Figure 8:
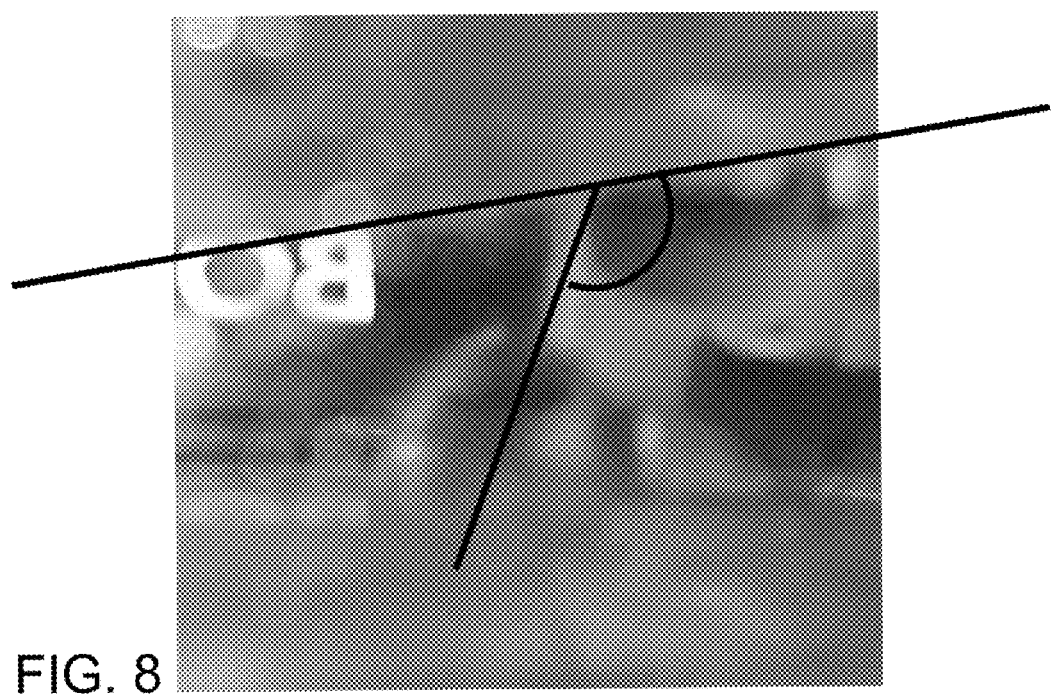
FIG. 8 is FIG. 6 labeled to show the contact angle.

FIG. 6 shows a droplet of hexadecane under a solution containing 1 wt % PEG1000 phosphate ester at a pH of 10 on a CaCO3 crystal. This shows the presence of PEG1000 phosphate ester, eases the contact angle of hexadecane on CaCO3. The pretreatment of calcium carbonate crystal was done by immersing the crystal in an aqueous solution of e.g. PEG1000 phosphate ester (e.g. 1 wt %, pH 9-10). A successful adsorption onto the crystal and a respective change of the surface properties is shown by measuring the contact angle of hexadecane. FIG. 8 is FIG. 6 labeled to show the contact angle. FIG. 8 shows the contact angle was >130°.

Comparison of FIGS. 7 and 8 shows the presence of PEG1000 phosphate ester onto the CaCO3 crystal increases the contact angle of hexadecane on CaCO3 from <80° to >130°.

Thus, a low contact angle is observed for the crystal in pure water (i.e. good adsorption of the oil onto the crystal, which is undesirable) and a high contact angle is observed for the crystal in a solution of water and PEG 1000 phosphate ester (i.e. poor adsorption of the oil onto the crystal, which is desirable).

It is apparent that embodiments other than those expressly described above come within the spirit and scope of the present claims. Thus, the present invention is not defined by the above description, but rather is defined by the claims appended hereto.

What is claimed is:

1. An oral care composition, comprising:
   (a) from about 10% to about 99% of at least one ingredient selected from the group consisting of a polishing agent (abrasive agent), sudsing agents (surfactants), a binder, a humectant, a medicinal agent, peroxide sources, alkali metal bicarbonate salts, thickening materials, titanium dioxide, flavor agents, sweetening agents, xylitol, coloring agents, water and mixtures thereof wherein the composition must contain at least one additive selected from the group consisting of a polishing agent (abrasive agent), sweetening agent, xylitol, flavor agent, anti-calculus agent, anti-caries agent and mixtures thereof, and
   (b) an effective amount of an anti-stain agent comprising:
   (b)(I)(1) organophosphorus compounds according to structure (I):

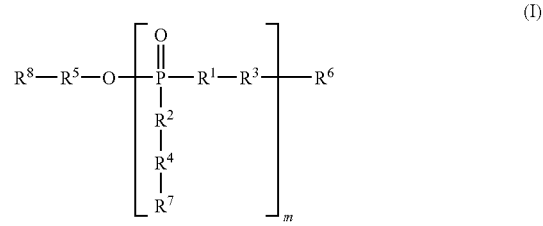

(I)

wherein:
each $R^1$ is and each $R^2$ is independently absent or O, provided that at least one of $R^1$ and $R^2$ is O,
each $R^3$ is independently alkyleneoxy, poly(alkyleneoxy), which may optionally, be substituted on one or more carbon atom of such alkyleneoxy, or poly (alkyleneoxy) group by hydroxyl, alkyl, hydroxyalkyl, alkoxy, alkenyl, aryl, or aryloxy,
$R^5$ is and each $R^4$ is independently absent or alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy, $R^6$ and $R^8$ are each and each $R^7$ is independently H, or $(C_1-C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, or —$POR^9R^{10}$, $R^9$ and $R^{10}$ are each independently hydroxyl, alkoxy, aryloxy, or $(C_1-C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, and m is an integer of from 1 to 5, (b)(I)(2) salts of organophosphorus compounds according to structure (I), (b)(I)(3) condensation reaction products of two or more molecules of one or more organophosphorus compounds according to structure (I), and (b)(I)(4) mixtures comprising two or more of the compounds, salts, and/or reaction products of (b)(I)(1), (b)(I)(2), and (b)(I)(3), wherein the anti-stain agent further comprises a vinyl alcohol material selected from:

(b)(II)(1) polymers comprising monomeric units according to structure (I-a):

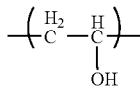

(I-a)

(b)(II)(2) salts of polymers (b)(II)(1), (b)(II)(3) reaction products of two or more molecules of one or more polymers (b)(II)(1).

2. The oral care composition of claim 1, further comprising sodium carbonate as a buffering agent.

3. The oral care composition of claim 2, comprising said polishing agent (abrasive agent), wherein said abrasive agent comprises an abrasive polishing material selected from the group consisting of silicas, aluminas, phosphates, orthophosphates, polymetaphosphates, beta calcium pyrophosphate, calcium carbonate, and mixtures thereof.

4. The oral care composition of claim 1, comprising about 0.01% to about 10% of a peroxide source.

5. The oral care composition of claim 1, wherein the organophosphorus material is present in a liquid carrier.

6. The oral care composition of claim 1, wherein the composition is a tooth cleaning product comprising a surfactant, a polishing agent (abrasive agent), and optionally, further comprising a liquid.

7. The oral care composition of claim 6, wherein the abrasive agent is an abrasive system comprising one or more of hydrated silica, colloidal silica, fumed silica, insoluble sodium metaphosphate, insoluble sodium aluminosilicates, sodium bicarbonate or mixtures thereof.

8. The oral care composition of claim 7, wherein the abrasive system is in amount of from about 5% to about 70% by weight of the tooth cleaning product.

9. The oral care composition of claim 6, wherein the tooth cleaning product is a toothpaste or a tooth cleaning gel.

10. The oral care composition of claim 6, wherein the liquid comprises one or more of water, humectant, binder, or a mixture thereof.

11. The oral care composition of claim 10, wherein the liquid is in an amount of from about 10% to about 90% by weight of the tooth cleaning product.

12. The oral care composition of claim 10, wherein the humectant is in an amount of from about 5% to about 85% of the tooth cleaning product.

13. The oral care composition of claim 10, wherein the tooth cleaning product is a translucent gel having a humectant to water ratio of at least about 0.5 to 1.

14. The oral care composition of claim 1, wherein the composition is a tooth powder comprising a polishing agent (abrasive agent), wherein the polishing agent is present in an amount of from about 20% to about 95% by weight of the composition.

15. The oral care composition of claim 14, wherein the effective amount of organophosphorus material is from about 0.1% to about 10% by weight of the tooth powder.

16. The oral care composition of claim 14, wherein the effective amount of organophosphorus material is from about 1% to about 5% by weight of said tooth powder.

17. The oral care composition of claim 14, comprising from over 50% to about 95% by weight polishing agent.

18. The oral care composition of claim 14, optionally further comprising one or more buffering agents or processing aids.

19. The oral care composition of claim 1, wherein the composition is a mouthwash comprising humectant, water, a member selected from the group consisting of a sweetening agent, xylitol, flavor agent and mixtures thereof, and further comprising an alcohol.

20. The oral care composition of claim 19, wherein the effective amount of the organophosphorus material is from about 0.1% to about 10% by weight of the mouthwash.

21. The oral care composition of claim 19, wherein the effective amount of the organophosphorus material is from about 1% to about 5% by weight of the mouthwash.

22. The oral care composition of claim 19, optionally further comprising one or more buffering agents or processing aids.

23. A toothpaste comprising the oral care composition of claim 1.

24. A chewing gum comprising the oral care composition of claim 1.

25. A mouthwash comprising the oral care composition of claim 1.

26. An oral care strip comprising the oral care composition of claim 1.

27. A lozenge comprising the oral care composition of claim 1.

28. A method for cleaning teeth comprising applying an effective amount of the composition of claim 1 to teeth in need of cleaning.

29. The oral care composition of claim 1, wherein the vinyl alcohol material has a weight average molecular weight of about 50,000 to 200,000, and a degree of hydrolysis of at least 88%.

30. The oral care composition of claim 29, wherein the vinyl alcohol material has a linear polymeric structure.

31. The oral care composition of claim 29, wherein the vinyl alcohol material has a branched polymeric structure.

32. The oral care composition of claim 29, wherein the vinyl alcohol material consists of monomeric units according to structure I-a.

33. The oral care composition of claim 29, wherein the vinyl alcohol material comprises monomeric units according to structure I-a and hydrophilic monomeric units other than the monomeric according to structure (I-a) selected from the group consisting of hydroxy($C_1$-$C_4$)alkyl (meth)acrylates, (meth)acrylamide, ($C_1$-$C_4$)alkyl (meth)acrylamides, N,N-dialkyl-acrylamides, alkoxylated (meth)acrylates, poly(ethylene glycol)-mono methacrylates and poly(ethyleneglycol)-monomethylether methacrylates, hydroxy($C_1$-$C_4$) acrylamides and methacrylamides, hydroxyl($C_1$-$C_4$)alkyl vinyl ethers, N-vinylpyrrole, N-vinyl-2-pyrrolidone, 2- and 4-vinylpyridine, ethylenically unsaturated carboxylic acids having a total of 3 to 5 carbon atoms, amino($C_1$-$C_4$alkyl, mono($C_1$-$C_4$)alkylamino($C_1$-$C_4$)alkyl, and di($C_1$-$C_4$)alkylamino($C_1$-$C_4$)alkyl (meth)acrylates, allyl alcohol, dimethylaminoethyl methacrylate, dimethylaminoethylmethacrylamide.

34. The oral care composition of claim 29, wherein the vinyl alcohol material comprises monomeric units according to structure I-a and hydrophobic monomeric units selected from the group consisting of ($C_1$-$C_{18}$)alkyl and ($C_5$-$C_{18}$)cycloalkyl (meth)acrylates, ($C_5$-$C_{18}$)alkyl(meth)acrylamides, (meth)acrylonitrile, vinyl ($C_1$-$C_{18}$)alkanoates, ($C_2$-$C_{18}$)alkenes, ($C_2$-$C_{18}$)haloalkenes, styrene, ($C_1$-$C_6$)alkylstyrenes, ($C_4$-$C_{12}$)alkyl vinyl ethers, fluorinated ($C_2$-$C_{10}$)alkyl (meth) acrylates, ($C_3$-$C_{12}$)perfluoroalkylethylthiocarbonylaminoethyl (meth)acrylates, (meth)acryloxyalkylsiloxanes, N-vinylcarbazole, ($C_1$-$C_{12}$) alkyl maleic, fumaric, itaconic, and mesaconic acid esters, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate, and 3-methacryloxypropylpentamethyldisiloxane.

* * * * *

UNITED STATES PATENT AND TRADEMARK OFFICE
CERTIFICATE OF CORRECTION

PATENT NO.         : 7,550,419 B2                                                          Page 1 of 1
APPLICATION NO.    : 12/137647
DATED              : June 23, 2009
INVENTOR(S)        : Tobias Johannes Fütterer, Lawrence Alan Hough and Robert Lee Reierson It is certified that error appears in the above-identified patent and that said Letters Patent is hereby corrected as shown below:

In the Claims

Claim 1, Column 24, line 42, cancel the text "(b) an effective amount of an anti-stain agent comprising:" and insert the following:
--(b) an effective amount of an anti-stain agent selected from the group consisting of:--

Signed and Sealed this
Twenty-second Day of July, 2014

Michelle K. Lee
*Deputy Director of the United States Patent and Trademark Office*